(12) United States Patent
Lyons et al.

(10) Patent No.: US 8,586,556 B2
(45) Date of Patent: Nov. 19, 2013

(54) METHODS, COMPOSITIONS AND DRUG DELIVERY SYSTEMS FOR INTRAOCULAR DELIVERY OF SIRNA MOLECULES

(75) Inventors: Robert T. Lyons, Laguna Hills, CA (US); Hongwen Ma Rivers, San Diego, CA (US); John T. Trogden, Villa Park, CA (US)

(73) Assignee: Allergan, Inc., Irvine, CA (US)

( * ) Notice: Subject to any disclaimer, the term of this patent is extended or adjusted under 35 U.S.C. 154(b) by 59 days.

(21) Appl. No.: 12/643,909

(22) Filed: Dec. 21, 2009

(65) Prior Publication Data

US 2010/0311808 A1    Dec. 9, 2010

Related U.S. Application Data

(63) Continuation-in-part of application No. 11/556,503, filed on Nov. 3, 2006, now Pat. No. 8,039,010.

(51) Int. Cl.
| | |
|---|---|
| *A61K 31/713* | (2006.01) |
| *A61P 27/06* | (2006.01) |
| *A61P 29/00* | (2006.01) |
| *A61P 27/02* | (2006.01) |
| *A61P 35/00* | (2006.01) |
| *A61P 31/04* | (2006.01) |

(52) U.S. Cl.
USPC ................................. 514/44 A; 514/44 R

(58) Field of Classification Search
None
See application file for complete search history.

(56) References Cited

U.S. PATENT DOCUMENTS

| | | |
|---|---|---|
| 4,521,210 A | 6/1985 | Wong |
| 4,853,224 A | 8/1989 | Wong |
| 4,997,652 A | 3/1991 | Wong |
| 5,164,188 A | 11/1992 | Wong |
| 5,443,505 A | 8/1995 | Wong |
| 5,501,856 A | 3/1996 | Ohtori |
| 5,766,242 A | 6/1998 | Wong |
| 5,824,072 A | 10/1998 | Wong |
| 5,869,079 A | 2/1999 | Wong |
| 6,074,661 A | 6/2000 | Olejnik |
| 6,248,345 B1 | 6/2001 | Goldenheim et al. |
| 6,331,313 B1 | 12/2001 | Wong |
| 6,369,116 B1 | 4/2002 | Wong |
| 6,699,493 B2 | 3/2004 | Wong |
| 6,713,081 B2 | 3/2004 | Robinson |
| 6,818,447 B1 | 11/2004 | Pavco |
| 6,899,717 B2 | 5/2005 | Weber |
| 7,048,946 B1 | 5/2006 | Wong |
| 7,090,681 B2 | 8/2006 | Weber |
| 7,468,065 B2 | 12/2008 | Lathrop et al. |
| 2004/0054374 A1 | 3/2004 | Weber |
| 2004/0138163 A1* | 7/2004 | McSwiggen et al. ........... 514/44 |
| 2004/0170665 A1 | 9/2004 | Donovan |
| 2005/0196421 A1 | 9/2005 | Hunter et al. |
| 2005/0203542 A1 | 9/2005 | Weber |
| 2005/0281861 A1 | 12/2005 | Hughes |
| 2006/0020044 A1 | 1/2006 | Berlin |
| 2006/0046961 A1 | 3/2006 | McKay et al. |
| 2006/0182783 A1 | 8/2006 | Hughes |
| 2006/0216242 A1 | 9/2006 | Rohloff et al. |
| 2007/0059336 A1 | 3/2007 | Hughes |
| 2008/0206341 A1* | 8/2008 | Gasco ......................... 424/489 |
| 2008/0268051 A1 | 10/2008 | Hughes et al. |
| 2009/0226531 A1 | 9/2009 | Lyons et al. |
| 2009/0258924 A1 | 10/2009 | Lyons et al. |

FOREIGN PATENT DOCUMENTS

WO    03/080648    10/2003

OTHER PUBLICATIONS

Thiel et al. (Oligonucleotides. Published online Aug. 5, 2009; 19(3): 209-222).*
Boehringer-Ingelheim (Specification Sheets for RG-752; Inherent Viscosity and MW for RG-752.
Carrasquillo K. et al., *Controlled delivery of the anti-VEGF aptamer EYE001 with poly(lactic-co-glycolic)acid microspheres*, IOVS Jan. 2003 44(1).
Gaudreault et al., *Preclinical pharmacokinetics of ranibizumab (rhuFabV2) after a single intravitreal administration*, IOVS, (2005); 46(2):726-733.
Heller, Biodegradable Polymers in Controlled Drug Delivery, In: CRC Critical Reviews in Therapeutic Drug Carrier Systems, vol. 1, CRC Press, Boca Raton, FL 1987, pp. 39-90.
Jackson J. et al., *The encapsulation of ribozymes in biodegradable polymeric matrices*, Int J of Pharmaceutics 243 (2002) 43-55.
Khan A. et al., *Sustained polymeric delivery of gene silencing antisense ODNs, siRNA, DNAzymes and ribozymes: in vitro and in vivo studies*, J Drug Target, Jul. 12, 2004(6), pp. 393-404.
Rosa G., et al., *A new delivery system for antisense therapy: PLGA microspheres encapsulating olignucleotide/polyethyleneimine solid complexes*, Int J of Pharmaceutics 254 (2003) 89-93.
Stone et al (N. Engl J. Med. Oct. 5, 2006, 355 (14) : 1493-1495.
Van Wijngaarden et al (JAMA, Mar. 23-30, 2005 ; 293(12) : 1509-1513.
International Search Report mailed May 22, 2012, PCT/US2010/059995, Allergan, Inc.

* cited by examiner

*Primary Examiner* — Scott Long
(74) *Attorney, Agent, or Firm* — Joel B. German; Debra D. Condino

(57) ABSTRACT

Biocompatible intraocular drug delivery systems in the form of an implant for intraocular administration of siRNA molecules. The drug delivery systems may be placed in an eye to treat or reduce the occurrence of one or more ocular conditions, such as retinal damage, including glaucoma and proliferative vitreoretinopathy among others.

8 Claims, 4 Drawing Sheets

Figure 5

5' B C U G A G U U U A A A A G G C A C C C T T B 3'   SEQ ID NO. 7   S (sense)
   | | | | | | | | | | | | | | | | | | |
3' T$_5$T G A C U C A A A U U U U C C G U G G G 5'   SEQ ID NO. 8   AS (antisense)

METHODS, COMPOSITIONS AND DRUG DELIVERY SYSTEMS FOR INTRAOCULAR DELIVERY OF SIRNA MOLECULES

CROSS REFERENCE TO RELATED APPLICATIONS

This application is a continuation-in-part of U.S. patent application Ser. No. 11/556,503 filed on Nov. 3, 2006, the entire disclosure of which is incorporated herein by reference.

BACKGROUND

The present invention generally relates to compositions, drug delivery systems and methods to treat an eye of a patient, and more specifically to drug delivery systems in the form of implants comprising short interfering ribonucleic acid (siRNA) molecules, and to methods of making and using such systems, for example, to treat or reduce one or more symptoms of an ocular condition to improve or maintain vision of a patient.

RNA has been used for several years to reduce or interfere with expression of targeted genes in a variety of systems. Although originally thought to require use of long double-stranded RNA (dsRNA) molecules, the active mediators of RNAi are now known to be short dsRNAs. Short single-stranded antisense RNA molecules were demonstrated to be effective inhibitors of gene expression more than a decade ago, but are susceptible to degradation by a variety of nucleases and are therefore of limited utility without chemical modification. Double-stranded RNAs are surprisingly stable and, unlike single-stranded DNA or antisense RNA oligonucleotides, do not need extensive modification to survive in tissue culture media or living cells.

Short interfering RNAs are naturally produced by degradation of long dsRNAs by Dicer, an RNase III class enzyme. While these fragments are usually about 21 bases long, synthetic dsRNAs of a variety of lengths, ranging from 18 bases to 30 bases (D.-H. Kim et al., *Synthetic dsRNA dicer-substrates enhance RNAi potency and efficacy,* 23 Nature Biotechnology 222-226 (2005)), can be used to suppress gene expression. These short dsRNAs are bound by the RNA Induced Silencing Complex (RISC), which contains several protein components including a ribonuclease that degrades the targeted mRNA. The antisense strand of the dsRNA directs target specificity of the RISC RNase activity, while the sense strand of an RNAi duplex appears to function mainly to stabilize the RNA prior to entry into RISC and is degraded or discarded after entering RISC.

Chemically synthesized RNAi duplexes have historically been made as two 21-mer oligonucleotides that form a 19-base RNA duplex with two deoxythymidine bases added as 3' overhangs. (S. M. Elbashir et al., *Functional anatomy of siRNAs for mediating efficient RNAi in Drosophila melanogaster embryo lysate,* 20 EMBO J. 6877-6888 (2001)). Blunt 19-mer duplexes can also be used to trigger RNAi in mammalian systems. (F. Czaudema, *Structural variations and stabilizing modifications of synthetic siRNAs in mammalian cells,* 31 Nucleic Acids Res. 2705-2716 (2003)). These blunt duplexes, however, are generally less potent. Blunt duplexes can be effectively used for longer RNAs that are Dicer substrates. D.-H. Kim et al., supra. In this case, the duplex is processed by Dicer to 21-mer length with 2-base 3'-overhangs before entry into RISC.

Relatively recently, researchers observed that double stranded RNA ("dsRNA") could be used to inhibit protein expression. This ability to silence a gene has broad potential for treating human diseases, and many researchers and commercial entities are currently investing considerable resources in developing therapies based on this technology.

It is generally considered that the major mechanism of RNA induced silencing (RNA interference, or RNAi) in mammalian cells is mRNA degradation. Initial attempts to use RNAi in mammalian cells focused on the use of long strands of dsRNA. However, these attempts to induce RNAi met with limited success, due in part to the induction of the interferon response, which results in a general, as opposed to a target-specific, inhibition of protein synthesis. Thus, long dsRNA is not a viable option for RNAi in mammalian systems.

More recently it has been shown that when short (18-30 bp) RNA duplexes are introduced into mammalian cells in culture, sequence-specific inhibition of target mRNA can be realized without inducing an interferon response. Certain of these short dsRNAs, referred to as small inhibitory RNAs ("siRNAs"), can act catalytically at sub-molar concentrations to cleave greater than 95% of the target mRNA in the cell. A description of the mechanisms for siRNA activity, as well as some of its applications are described in Provost et al. (2002) Ribonuclease Activity and RNA Binding of Recombinant Human Dicer, EMBO J. 21(21): 5864-5874; Tabara et al. (2002).

From a mechanistic perspective, introduction of long double stranded RNA into plants and invertebrate cells is broken down into siRNA by a Type III endonuclease known as Dicer. Sharp, RNA interference—2001, Genes Dev. 2001, 15:485. Dicer, a ribonuclease-III-like enzyme, processes the dsRNA into 19-23 base pair short interfering RNAs with characteristic two base 3' overhangs. Bernstein, Gaudy, Hammond, & Hannon (2001) Role for a bidentate ribonuclease in the initiation step of RNA interference, Nature 409:363. The siRNAs are then incorporated into an RNA-induced silencing complex (RISC) where one or more helicases unwind the siRNA duplex, enabling the complementary antisense strand to guide target recognition. Nykanen, Haley, & Zamore (2001) ATP requirements and small interfering RNA structure in the RNA interference pathway, Cell 107:309. Upon binding to the appropriate target mRNA, one or more endonucleases within the RISC cleaves the target to induce silencing. (Elbashir, Lendeckel, & Tuschl (2001) RNA interference is mediated by 21- and 22-nucleotide RNAs, Genes Dev. 15:188, FIG. 1).

The interference effect can be long lasting and may be detectable after many cell divisions. Moreover, RNAi exhibits sequence specificity. Kisielow, M. et al. (2002) Isoform-specific knockdown and expression of adaptor protein ShcA using small interfering RNA, J. Biochem. 363:1-5. Thus, the RNAi machinery can specifically knock down one type of transcript, while not affecting closely related mRNA. These properties make siRNA a potentially valuable tool for inhibiting gene expression and studying gene function and drug target validation. Moreover, siRNAs are potentially useful as therapeutic agents against: (1) diseases that are caused by over-expression or misexpression of genes; and (2) diseases brought about by expression of genes that contain mutations.

Intravitreal implants have been described which include non-macromolecule therapeutic agents. For example, U.S. Pat. No. 6,713,081 discloses ocular implant devices made from polyvinyl alcohol and used for the delivery of a therapeutic agent to an eye in a controlled and sustained manner. The implants may be placed subconjunctivally or intravitreally in an eye.

Biocompatible implants for placement in the eye have also been disclosed in a number of patents, such as U.S. Pat. Nos.

4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493. U.S. Patent Publication No. 20040170665 describes implants which include a Clostridial neurotoxin. Useful implants are also described in US 2005/0281861 and US 2006/0182783. United States patent applications which disclose therapeutic use of a siRNA include Ser. Nos. 11/116,698; 11/370,301; 11/742,350, and; 12/044,889. The contents of all of these applications are incorporated herein by reference in their entireties.

It would be advantageous to provide eye implantable drug delivery systems, such as intraocular implants, and methods of using such systems, that are capable of releasing a macromolecule therapeutic agent comprising a siRNA at a sustained or controlled rate for extended periods of time and in amounts with few or no negative side effects.

SUMMARY

The present invention provides new drug delivery systems, and methods of making and using such systems, for administering siRNA molecules to an eye, for example, to achieve one or more desired therapeutic effects. The drug delivery systems are in the form of implants or implant elements that may be placed in an eye. The present systems and methods advantageously provide for extended release times of one or more siRNA therapeutic agents. Thus, the patient in whose eye the system has been placed receives a therapeutic amount of an agent for a long or extended time period without requiring additional administrations of the agent. For example, the patient has a substantially consistent level of therapeutically active agent available for consistent treatment of the eye over a relatively long period of time, for example, on the order of at least about one week, such as between about one and about twelve months after receiving an implant. Such extended release times facilitate obtaining successful treatment results while reducing problems associated with existing techniques.

Intraocular drug delivery systems in accordance with the disclosure herein comprise a therapeutic component and a drug release sustaining component associated with the therapeutic component. The therapeutic component comprises at least one siRNA molecule, and the drug release sustaining component comprises a biodegradable polymer, a biodegradable co-polymer, or combinations thereof.

The polymeric component of the present systems may comprise a polymer and/or a copolymer and/or a block co-polymer selected from the group consisting of poly-lactic acid (PLA), poly-glycolic acid (PGA), poly-lactide-co-glycolide (PLGA) (e.g. R203H), polyesters, poly (ortho ester), poly(phosphazine), poly (phosphate ester), polyethylene glycol (PEG), triblock copolymers polycaprolactones, gelatin, collagen, poly(D,L-lysine), derivatives thereof, and combinations thereof.

In accordance with the present invention, the therapeutic component of the present systems can comprise, consist essentially of, or consist entirely of, short interfering ribonucleic acids (siRNAs, also referred to as small interfering RNAs). Advantageously, the therapeutic agent is released in a biologically active form when the implant is placed in an eye.

The polymeric component of the present systems may comprise a polymer selected from the group consisting of poly-lactic acid (PLA), poly-glycolic acid (PGA), poly-lactide-co-glycolide (PLGA), polyesters, poly(ortho ester), poly (phosphazine), poly(phosphate ester), polycaprolactones, gelatin, collagen, derivatives thereof, and combinations thereof.

A method of making the present systems involves combining or mixing the therapeutic component with the polymeric component to form a mixture. The mixture may then be extruded or compressed to form a single composition. The single composition may then be processed to form individual implants suitable for placement in an eye of a patient.

The implants may be placed in an ocular region to treat a variety of ocular conditions, such as treating, preventing, or reducing at least one symptom associated with glaucoma, or ocular conditions related to excessive excitatory activity or glutamate receptor activation or associated with, for example, retinal neurodegeneration, such as by apoptosis or necrosis, and angiogenesis, such as in conditions such as exudative and non-exudative age related macular degeneration. Placement of the implants may be through surgical implantation, or through the use of an implant delivery device which administers the implant via a needle or catheter. The implants can effectively treat conditions associated with neovascularization of the eye, such as the retina. The therapeutic component can be released at controlled or predetermined rates when the implant is placed in the eye. Such rates may range from about 0.003 micrograms/day to about 5000 micrograms/day.

Kits in accordance with the present invention may comprise one or more of the present systems, and instructions for using the systems. For example, the instructions may explain how to administer the present drug delivery systems to a patient, and types of conditions that may be treated with the systems.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description, examples, and claims, particularly when considered in conjunction with the accompanying drawings.

BRIEF DESCRIPTION OF THE DRAWINGS

FIG. 5 shows the sequence and duplex structure of Sima-027.

DESCRIPTION

Figure 1:
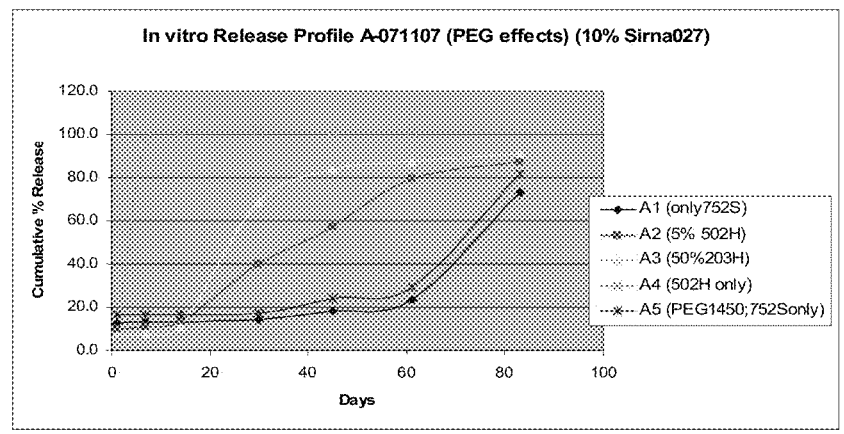
FIGS. 1-4 show the in vitro release profiles for products according to the invention comprising Sima027 as the therapeutic component.

As described herein, controlled and sustained administration of one or more therapeutic agents through the use of one or more intraocular drug delivery systems, such as intraocular implants, may effectively treat one or more undesirable ocular conditions. The present drug delivery systems comprise a pharmaceutically acceptable polymeric composition and are formulated to release one or more pharmaceutically active agents over an extended period of time, such as for more than one week, and in certain embodiments for a period of time of one year or more. In other words, the present drug delivery systems comprise a polymeric component and a therapeutic component. As described herein, the polymeric component can comprise one or more biodegradable polymers, one or more biodegradable copolymers, one or more non-biodegradable polymers, and one or more non-biodegradable copolymers, and combinations thereof. The polymeric component may be understood to be a drug release sustaining component.

The therapeutic component of the present drug delivery systems may comprise, consist essentially of, or consist entirely of, one or more therapeutic agents selected from small interfering ribonucleic acid (siRNA) molecules. The present systems are effective to provide a therapeutically effective dosage(s) of the agent or agents directly to a region of the eye to treat, prevent, and/or reduce one or more symptoms of one or more undesirable ocular conditions. Thus, with each administration, therapeutic agents will be made available at the site where they are needed and will be maintained at effective concentrations for an extended period of time, rather than subjecting the patient to more frequent injections or, in the case of self-administered drops, ineffective treatment with only limited bursts of exposure to the active agent or agents or, in the case of systemic administration, higher systemic exposure and concomitant side effects or, in the case of non-sustained release dosages, potentially toxic transient high tissue concentrations associated with pulsed, non-sustained release dosing.

1. DEFINITIONS

For the purposes of this description, we use the following terms as defined in this section, unless the context of the word indicates a different meaning.

As used herein, an "intraocular drug delivery system" refers to a device or element that is structured, sized, or otherwise configured to be placed in an eye. The present drug delivery systems are generally biocompatible with physiological conditions of an eye and do not cause unacceptable or undesirable adverse side effects. The present drug delivery systems may be in the form of implants and may be placed in an eye without disrupting vision of the eye.

As used herein, a "therapeutic" component" refers to a portion of a drug delivery system comprising one or more therapeutic agents, active ingredients, or substances used to treat a medical condition of the eye. The therapeutic component is typically homogenously distributed throughout the nanoparticles. The therapeutic agents of the therapeutic component are typically ophthalmically acceptable, and are provided in a form that does not cause adverse reactions when the implant is placed in an eye. As discussed herein, the therapeutic agents can be released from the drug delivery systems in a biologically active form. For example, the therapeutic agents may retain their three dimensional structure when released from the system into an eye.

As used herein, a "drug release sustaining component" refers to a portion of the drug delivery system that is effective in providing a sustained release of the therapeutic agents of the systems. A drug release sustaining component may be a biodegradable polymer matrix, or it may be a coating covering a core region of a nanoparticle that comprises a therapeutic component.

As used herein, "associated with" means mixed with, dispersed within, coupled to, covering, or surrounding.

As used herein, an "ocular region" or "ocular site" refers generally to any area of the eyeball, including the anterior and posterior segment of the eye, and which generally includes, but is hot limited to, any functional (e.g., for vision) or structural tissues found in the eyeball, or tissues or cellular layers that partly or completely line the interior or exterior of the eyeball. Specific examples of areas of the eyeball in an ocular region include, but are not limited to, the anterior chamber, the posterior chamber, the vitreous cavity, the choroid, the suprachoroidal space, the subretinal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris; the posterior chamber (behind the iris. but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, retinal pigmented epithelium, Bruch's membrane, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal. vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "biodegradable polymer" refers to a polymer or polymers which degrade in vivo, and wherein erosion of the polymer or polymers over time occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

The term "treat", "treating", or "treatment" as used herein, refers to reduction or resolution or prevention of an ocular condition, ocular injury or damage, or to promote healing of injured or damaged ocular tissue. The term "therapeutically effective amount" as used herein, refers to the level or amount of agent needed to treat an ocular condition, or reduce or prevent ocular injury or damage without causing significant negative or adverse side effects to the eye or a region of the eye. Intraocular drug delivery systems have been developed which can release drug loads over various' time periods. These systems, which when placed into an eye of an individual, such as the vitreous of an eye, provide therapeutic levels of a macromolecule therapeutic agent for extended periods of time (e.g., for about one week or more). In certain embodiments, the macromolecule therapeutic agent is an siRNA having at least one property selected from the group consisting of anti-angiogenesis, ocular hemorrhage treatment, non-steroidal anti-inflammatory, growth factor (e.g. VEGF) inhibitor, growth factor, cytokines and antibiotics. The disclosed systems are effective in treating ocular conditions, such as posterior ocular conditions, such as glaucoma and neovascularization, and generally improving or maintaining vision in an eye.

The phrase "gene silencing" refers to a process by which the expression of a specific gene product is lessened or attenuated. Gene silencing can take place by a variety of pathways. Unless specified otherwise, as used herein, gene silencing refers to decreases in gene product expression that results from RNA interference (RNAi), a defined, though partially characterized pathway whereby small inhibitory RNA (siRNA) act in concert with host proteins (e.g., the RNA induced silencing complex, RISC) to degrade messenger RNA (mRNA) in a sequence-dependent fashion. The level of gene silencing can be measured by a variety of means, including, but not limited to, measurement of transcript levels by Northern Blot Analysis, B-DNA techniques, transcription-sensitive reporter constructs, expression profiling (e.g., DNA chips), and related technologies. Alternatively, the level of silencing can be measured by assessing the level of the protein encoded by a specific gene. This can be accomplished by performing a number of studies including Western Analysis, measuring the levels of expression of a reporter protein that has e.g., fluorescent properties (e.g., GFP) or enzymatic activity (e.g., alkaline phosphatases), or several other procedures.

The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

The term "treat", "treating", or "treatment" as used herein, refers to reduction or resolution or prevention of an ocular condition, ocular injury or damage, or to promote healing of injured or damaged ocular tissue.

The term "therapeutically effective amount" as used herein, refers to the level or amount of agent needed to treat an ocular condition, or reduce or prevent ocular injury or damage without causing significant negative or adverse side effects to the eye or a region of the eye.

2. COMPONENTS OF THE DRUG DELIVERY SYSTEM 2.1 The Therapeutic Component

As noted above, the therapeutic component of the drug delivery system comprises at least one siRNA molecule. Various types and kinds of siRNA molecules are per se known to those skilled in the art, and known for treatment of various biological and pharmacological conditions. siRNA molecules may be divided into five (5) groups (non-functional, semi-functional, functional, highly functional, and hyper-functional) based on the level or degree of silencing that they induce in cultured cell lines. As used herein, these definitions are based on a set of conditions where the siRNA is transfected into said cell line at a concentration of 100 nM and the level of silencing is tested at a time of roughly 24 hours after transfection, and not exceeding 72 hours after transfection. In this context, "non-functional siRNA" are defined as those siRNA that induce less than 50% (<50%) target silencing. "Semi-functional siRNA" induce 50-79% target silencing. "Functional siRNA" are molecules that induce 80-95% gene silencing. "Highly-functional siRNA" are molecules that induce greater than 95% gene silencing. "Hyperfunctional siRNA" are a special class of molecules. For purposes of this document, hyperfunctional siRNA are defined as those molecules that: (1) induce greater than 95% silencing of a specific target when they are transfected at subnanomolar concentrations (i.e., less than one nanomolar); and/or (2) induce functional (or better) levels of silencing for greater than 96 hours. These relative functionalities (though not intended to be absolutes) may be used to compare siRNAs to a particular target for applications such as functional genomics, target identification and therapeutics.

In some preferred embodiments of the present drug delivery systems, the siRNA has a nucleotide sequence that is effective in inhibiting cellular production of vascular endothelial growth factor (VEGF) or VEGF receptors. VEGF is a endothelial cell mitogen (Connolly D. T., et al., Tumor vascular permeability factor stimulates endothelial cell growth and angiogenesis. J. Clin. Invest. 84: 1470-1478 (1989)), that through binding with its receptor, VEGFR, plays an important role in the growth and maintenance of vascular endothelial cells and in the development of new blood- and lymphatic-vessels (Aiello L. P., et al., Vascular endothelial growth factor in ocular fluid of patients with diabetic retinopathy and other retinal disorders, New Engl. J. Med. 331: 1480-1487 (1994)).

Currently, the VEGF receptor family is believed to consist of three types of receptors, VEGFR-1 (Flt-1), VEGFR-2 (KDR/Flk-1) and VEGFR-3 (Flt-4), all of which belong to the receptor type tyrosine kinase superfamily (Mustonen T. et al., Endothelial receptor tyrosine kinases involved in angiogenesis, J. Cell Biol. 129: 895-898 (1995)). Among these receptors, VEGFR-1 appears to bind the strongest to VEGF, VEGFR-2 appears to bind more weakly than VEGFR-1, and VEGFR-3 shows essentially no binding, although it does bind to other members of the VEGF family. The tyrosine kinase domain of VEGFR-1, although much weaker than that of VEGFR-2, transduces signals for endothelial cells. Thus, VEGF is a substance that stimulates the growth of new blood vessels. The development of new blood vessels, neovascularization or angiogenesis, in the eye is believed to cause loss of vision in wet macular degeneration and other ocular conditions, including edema.

Sustained release drug delivery systems which include active siRNA molecules can release effective amounts of active siRNA molecules that associate with a ribonuclease complex (RISC) in target cells to inhibit the production of a target protein, such as VEGF or VEGF receptors. The siRNA of the present systems can be double-stranded or single stranded RNA molecules and may have a length less than about 50 nucleotides, less than about 40 nucleotides, less than about 30 nucleotides, less than about 20 nucleotides or less than 10 nucleotides. In certain embodiments, the systems may comprise a siRNA having a hairpin structure, and thus may be understood to be a short hairpin RNA (shRNA), as available from Invitrogen (San Diego, Calif.).

Some siRNAs that are used in the present systems preferably inhibit production of VEGF or VEGF receptors compared to other cellular proteins. In certain embodiments, the siRNAs can inhibit production of VEGF or VEGFR by at least 50%, preferably by at least 60%, and more preferably by about 70% or more. Thus, these siRNAs have nucleotide sequences that are effective in providing these desired ranges of inhibition.

The nucleotide sequence of the human VEGF isoform, VEGF 165 is identified as SEQ ID NO: 1, below. The nucleotide sequence has a GenBank Accession Number AB021221.

```
                                              (SEQ ID NO: 1)
atgaactttctgctgtcttgggtgcattggagccttgccttgctgctcta cctccaccatgccaagtggtcccaggctgcacccatggcagaaggaggag ggcagaatcatcacgaagtggtgaagttcatggatgtctatcagcgcagc tactgccatccaatcgagaccctggtggacatcttccaggagtaccctga tgagatcgagtacatcttcaagccatcctgtgtgccctgatgcgatgcg ggggctgctgcaatgacgagggcctggagtgtgtgcccactgaggagtcc aacatcaccatgcagattatgcggatcaaacctcaccaaggccagcacat aggagagatgagcttcctacagcacaacaaatgtgaatgcagaccaaga aagatagagcaagacaagaaatccctgtgggccttgctcagagcggaga aagcatttgtttgtacaagatccgcagacgtgtaaatgttcctgcaaaaa cacagactcgcgttgcaaggcgaggcagcttgagttaaacgaacgtactt gcagatgtgacaagccgaggcggtga
```

The nucleotide sequence of human VEGFR2 is identified as SEQ ID NO: 2, below. The nucleotide sequence has a GenBank Accession Number AF063658.

```
                                              (SEQ ID NO: 2)
atggagagcaaggtgctgctggccgtcgccctgtggctctgcgtggagac ccgggccgcctctgtgggtttgcctagtgtttctcttgatctgcccaggc tcagcatacaaaaagacatacttacaattaaggctaatacaactcttcaa attacttgcaggggacagagggacttggactggctttggcccaataatca gagtggcagtgagcaaaggtggaggtgactgagtgcagcgatggcctct tctgtaagacactcacaattccaaaagtgatcggaaatgacactggagcc tacaagtgcttctaccgggaaactgacttggcctcggtcatttatgtcta tgttcaagattacagatctccatttattgcttctgttagtgaccaacatg gagtcgtgtacattactgagaacaaaaacaaaactgtggtgattccatgt ctcgggtccatttcaaatctcaacgtgtcactttgtgcaagatacccaga aaagagatttgttcctgatggtaacagaatttcctgggacagcaagaagg gctttactattcccagctacatgatcagctatgctggcatggtcttctgt gaagcaaaaattaatgatgaaagttaccagtctattatgtacatagttgt cgttgtagggtataggatttatgatgtggttctgagtccgtctcatggaa ttgaactatctgttggagaaaagcttgtcttaaattgtacagcaagaact gaactaaatgtggggattgacttcaactgggaatacccttcttcgaagca tcagcataagaaacttgtaaaccgagacctaaaaacccagtctgggagtg agatgaagaaatttttgagcaccttaactatagatggtgtaacccggagt gaccaaggattgtacacctgtgcagcatccagtgggctgatgaccaagaa gaacagcacatttgtcagggtccatgaaaaaccttttgttgcttttggaa gtggcatggaatctctggtggaagccacggtgggggagcgtgtcagaatc cctgcgaagtaccttggttacccaccccagaaataaaatggtataaaaa tggaatacccttgagtccaatcacacaattaaagcggggcatgtactga cgattatggaagtgagtgaaagagacacaggaaattacactgtcatcctt accaatcccatttcaaaggagaagcagagccatgtggtctctctggttgt gtatgtcccaccccagattggtgagaaatctctaatctctcctgtggatt cctaccagtacggcaccactcaaacgctgacatgtacggtctatgccatt cctccccgcatcacatccactggtattggcagttggaggaagagtgcgc caacgagcccagccaagctgtctcagtgacaaacccataccttgtgaag aatggagaagtgtggaggacttccagggagggaaataaaattgaagttaat aaaaatcaattgctctaattgaaggaaaaaacaaaactgtaagtaccct tgttatccaagcggcaaatgtgtcagctttgtacaaatgtgaagcggtca acaaagtcgggagaggagagagggtgatctccttccacgtgaccaggggt cctgaaattactttgcaacctgacatgcagcccactgagcaggagagcgt gtctttgtggtgcactgcagacagatctacgtttgagaacctcacatggt acaagcttggcccacagcctctgccaatccatgtgggagagttgcccaca cctgtttgcaagaacttggatactctttggaaattgaatgccaccatgtt ctctaatagcacaaatgacattttgatcatggagcttaagaatgcatcct tgcaggaccaaggagactatgtctgccttgctcaagacaggaagaccaag aaaagacattgcgtggtcaggcagctcacagtcctagagcgtgtggcacc cacgatcacaggaaacctggagaatcagacgacaagtattggggaaagca tcgaagtctcatgcacggcatctgggaatcccctccacagatcatgtgg tttaaagataatgagaccttgtagaagactcaggcattgtattgaagga tgggaaccggaacctcactatccgcagagtgaggaaggaggacgaaggcc tctacacctgccaggcatgcagtgttcttggctgtgcaaaagtggaggca tttttcataatagaaggtgcccaggaaaagacgaacttggaaatcattat
```

-continued

```
tctagtaggcacggcggtgattgccatgttcttctggctacttcttgtca
tcatcctacggaccgttaagcgggccaatggaggggaactgaagacaggc
tacttgtccatcgtcatggatccagatgaactcccattggatgaacattg
tgaacgactgccttatgatgccagcaaatgggaattccccagagaccggc
tgaagctaggtaagcctcttggccgtggtgcctttggccaagtgattgaa
gcagatgcctttggaattgacaagacagcaacttgcaggacagtagcagt
caaaatgttgaaagaaggagcaacacacagtgagcatcgagctctcatgt
ctgaactcaagatcctcattcatattggtcaccatctcaatgtggtcaac
cttctaggtgcctgtaccaagccaggagggccactcatggtgattgtgga
attctgcaaatttggaaacctgtccacttacctgaggagcaagagaaatg
aatttgtcccctacaagaccaaaggggcacgattccgtcaagggaaagac
tacgttggagcaatccctgtggatctgaaacggcgcttggacagcatcac
cagtagccgagctcagccagctctggatttgtggaggagaagtccctca
gtgatgtagaagaagaggaagctcctgaagatctgtataaggacttcctg
accttggagcatctcatctgttacagcttccaagtggctaagggcatgga
gttcttggcatcgcgaaagtgtatccacagggacctggcggcacgaaata
tcctcttatcggagaagaacgtggttaaaatctgtgactttggcttggcc
cgggatatttataaagatccagattatgtcagaaaaggagatgctcgcct
cccttgaaatggatggccccagaaacaatttttgacagagtgtacacaa
tccagagtgacgtctggtcttttggtgttttgctgtgggaaatattttcc
ttaggtgcttctccatatcctggggtaaagattgatgaagaattttgtag
gcgattgaaagaaggaactagaatgagggcccctgattatactacaccag
aaatgtaccagaccatgctggactgctggcacggggagcccagtcagaga
cccacgttttcagagttggtggaacatttgggaaatctcttgcaagctaa
tgctcagcaggatggcaaagactacattgttcttccgatatcagagactt
tgagcatggaagaggattctggactctctctgcctacctcacctgtttcc
tgtatggaggaggaggaagtatgtgacccccaaattccattatgacaacac
agcaggaatcagtcagtatctgcagaacagtaagcgaaagagccggcctg
tgagtgtaaaaacatttgaagatatcccgttagaagaaccagaagtaaaa
gtaatcccagatgacaaccagacggacagtggtatggttcttgcctcaga
agagctgaaaactttggaagacagaaccaaattatctccatctttggtg
gaatggtgcccagcaaaagcagggagtctgtggcatctgaaggctcaaac
cagacaagcggctaccagtccggatatcactccgatgacacagacaccac
cgtgtactccagtgaggaagcagaacttttaaagctgatagagattggag
tgcaaaccggtagcacagcccagattctccagcctgactcggggaccaca
ctgagctctcctcctgtttaa
```

One specific example of a useful siRNA available from Acuity Pharmaceuticals (Pennsylvania) or Avecia Biotechnology under the name Cand5. Cand5 is a therapeutic agent that essentially silences the genes that produce VEGF. Thus, drug delivery systems including an siRNA selective for VEGF can prevent or reduce VEGF production in a patient in need thereof. The 5' to 3' nucleotide sequence of the sense strand of Cand5 is identified in SEQ ID NO: 3 below; and the 5' to 3' nucleotide sequence of the anti-sense strand of Cand5 is identified in SEQ ID NO: 4 below.

```
ACCUCACCAAGGCCAGCACdTdT      (SEQ ID NO: 3)

GUGCUGGCCUUGGUGAGGUdTdT      (SEQ ID NO: 4)
```

Another example of a useful siRNA available from Sima Therapeutics, a division of Merck & Co., Inc., under the name Sima-027. Sima-027 is a chemically modified short interfering RNA (siRNA) that targets vascular endothelial growth factor receptor-1 (VEGFR-1). Some additional examples of nucleic acid molecules that modulate the synthesis, expression and/or stability of an mRNA encoding one or more receptors of vascular endothelial growth factor are disclosed in U.S. Pat. No. 6,818,447 (Pavco).

Sima-027 is the designation for a double stranded siRNA that consists of a sense and antisense strand duplexed through base pairing, wherein the sense strand has the sequence CUGAGUUUAAAAGGCACCCdTdT (SEQ ID NO. 5), and the antisense strand has the sequence GGGUGCCUUUUAAACUCAGdTdT) (SEQ ID NO. 6). (See for example, WO 2007/133800). The sense strand is capped at the 3'- and 5'-ends with inverted 2'-deoxy abasic nucleotides. The Sima identifier for the sense strand is 31270. The antisense strand is capped at the 3'-end with two 2'-deoxythymidine nucleosides connected through a phosphorothioate linkage. The Sima identifier for the antisense strand is 31273. The chemical name for each strand of the duplex is g Sense Strand:

1,2-Dideoxy-P-ribofuranosylyl-(5'→5')-P-cytidylyl-(3'→5')-P-uridylyl-(3'→5')-P-guanylyl-(3'→5')-P-adenylyl-(3'→5')-P-guanylyl-(3'→5')-P-uridylyl-(3'→5')-P-uridylyl-(3'→5')-P-uridylyl-(3'→5')-P-adenylyl-(3'→5')-P-adenylyl-(3'→5')-P-adenylyl-(3'→5')-P-adenylyl-(3'→5')-P-guanylyl-(3'→5')-P-guanylyl-(3'→5')-P-cytidylyl-(3'→5')-P-adenylyl-(3'→5')-P-cytidylyl-(3'→5')-P-cytidylyl-(3'→5')-P-cytidylyl-(3'→5')-2'-deoxy-P-thymidylyl-(3'→5')-2'-deoxy-P-thymidylyl-(3'→3')-1,2-deoxyribofuranose Antisense Strand:

Guanylyl-(3'→5')-P-guanylyl-(3'→5')-P-guanylyl-(3'→5')-P-uridylyl-(3'→5')-P-guanylyl-(3'→5')-P-cytidylyl-(3'→5')-P-cytidylyl-(3'→5')-P-uridylyl-(3'→5')-P-uridylyl-(3'→5')-P-uridylyl-(3'→5')-P-uridylyl-(3'→5')-P-adenylyl-(3'→5')-P-adenylyl-(3'→5')-P-adenylyl-(3'→5')-P-cytidylyl-(3'→5')-P-uridylyl-(3'→5')-P-cytidylyl-(3'→5')-P-adenylyl-(3'→5')-P-guanylyl-(3'→5')-P-2'-deoxythymidylyl-(3'→5')-P-thio-2'-deoxythymidine Table 1 provides a summary of the characteristics of Sima-027.

TABLE 1

Brief description of Sirna-027

| Descriptor | Sense Strand | Antisense Strand |
| --- | --- | --- |
| 5'-3' Structural Formula | BCUGAGUUUAAAAGGCACCCTTB (SEQ ID NO. 7) | GGGUGCCUUUUAAACUCAGT$_s$T (SEQ ID NO. 8) |
| Empirical Formula | $C_{211}H_{269}N_{77}O_{153}P_{22}$ | $C_{200}H_{249}N_{73}O_{146}P_{20}S$ |
| Molecular Weight | 7013.13 (H$^+$ form) | 6662.96 (H$^+$ form) |

FIG. 5 shows the Sequence and duplex structure of Sirna-027. The two oligonucleotide strands of the siRNA duplex are shown with base pairing between ribonucleotides of the sense (S) and antisense (AS) strand indicated as dashes. Modifications are unpaired deoxythymidines (T), one phosphorothioate linkage (s) and two inverted 2'-deoxy abasic nucleotides (B). The ribonucleotides are adenosine (A), guanosine (G), uridine (U), and cytidine (C).

Thus, the present drug delivery systems may comprise a VEGF or VEGFR inhibitor that includes an siRNA having a nucleotide sequence that is substantially identical to the nucleotide sequence of Cand5 or Sima-027, identified above. For example, the nucleotide sequence of an siRNA may have at least about 80% sequence homology to the nucleotide sequence of Cand5 or Sima-027 siRNAs. Preferably, a siRNA has a nucleotide sequence homology of at least about 90%, and more preferably at least about 95% of the Cand5 or Sima-027 siRNAs. In other embodiments, the siRNA may have a homology to VEGF or VEGFR that results in the inhibition or reduction of VEGF or VEGFR synthesis.

2.2 The Polymeric Component

As discussed herein, the polymeric component of the present drug delivery systems can comprise a polymer selected from the group consisting of biodegradable polymers, non-biodegradable polymers, biodegradable copolymers, non-biodegradable copolymers, and combinations thereof. In certain preferred embodiments, the polymer is selected from the group consisting of poly-lactic acid (PLA), poly-glycolic acid (PGA), poly-lactide-co-glycolide (PLGA), polyesters, poly(ortho ester), poly(phosphazine), poly(phosphate ester), polycaprolactones, gelatin, collagen, derivatives thereof, and combinations thereof.

The present drug delivery systems may be in the form of a solid element, a semisolid element, or a viscoelastic element, or combinations thereof. For example, the present systems may comprise one or more solid, semisolid, and/or viscoelastic implants or microparticles.

The therapeutic agent may be in a particulate or powder form and entrapped by a biodegradable polymer matrix. Usually, therapeutic agent particles in intraocular implants will have an effective average size less than about 3000 nanometers. However, in other embodiments, the particles may have an average maximum size greater than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers. In addition, when such particles are combined with a polymeric component, the resulting polymeric intraocular particles may be used to provide a desired therapeutic effect.

The therapeutic agent of the present systems is preferably from about 1% to 90% by weight of the drug delivery system. More preferably, the therapeutic agent is from about 5% to about 15% by weight of the system. In a preferred embodiment, the therapeutic agent comprises about 10% by weight of the system. In another embodiment, the therapeutic agent comprises about 20% by weight of the system.

Suitable polymeric materials or compositions for use in the implant include those materials which are compatible, that is biocompatible, with the eye so as to cause no substantial interference with the functioning or physiology of the eye. Such materials preferably include polymers that are at least partially and more preferably substantially completely biodegradable or bioerodible.

In addition to the foregoing, examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxocarbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 24 hours, preferably greater than about one month, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Also important to controlling the biodegradation of the polymer and hence the extended release profile of the drug delivery systems is the relative average molecular weight of the polymeric composition employed in the present systems. Different molecular weights of the same or different polymeric compositions may be included in the systems to modulate the release profile. In certain systems, the relative average molecular weight of the polymer will range from about 9 to about 64 kD, usually from about 10 to about 54 kD, and more usually from about 12 to about 45 kD.

In some drug delivery systems, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the system, where a more flexible system or implant is desirable for larger geometries. The % of polylactic acid in the polylactic acid polyglycolic acid (PLGA) copolymer can be 0-100%, preferably about 15-85%, more preferably about 35-65%. In some systems, a 50/50 PLGA copolymer is used.

The biodegradable polymer matrix of the present systems may comprise a mixture of two or more biodegradable polymers. For example, the system may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or a combination of both. It may be understood that the polymeric component of the present systems is associated with the therapeutic component so that the release of the therapeutic component into the eye is by one or more of diffusion, erosion, dissolution, and osmosis. As discussed herein, the matrix of an intraocular drug delivery system may release drug at a rate effective to sustain release of an amount of the therapeutic agent for more than one week after implantation into an eye. In certain systems, therapeutic amounts of the therapeutic agent are released for more than about one month, and even for about twelve months or more. For example, the therapeutic component can be released into the eye for a time period from about ninety days to about one year after the system is placed in the interior of an eye.

The release of the therapeutic agent from the intraocular systems comprising a biodegradable polymer matrix may include an initial burst of release followed by a gradual increase in the amount of the therapeutic agent released, or the release may include an initial delay in release of the therapeutic agent followed by an increase in release. When the system is substantially completely degraded, the percent of the therapeutic agent that has been released is about one hundred. Compared to existing implants, the systems disclosed herein do not completely release, or release about 100% of the therapeutic agent, until after about one week of being placed in an eye.

In one aspect of the invention, release profiles of the therapeutic agent are modified by inclusion in the polymeric component of release modifying excipient. Suitable excipients are alcohols, such as cholesterol, fatty alcohols, glycols and polysaccharides. Useful glycols include propylene glycol, dipropylene glycol, polypropylene glycol, polyethylene glycol (PEG), sorbitol and glycerol. In this regard, polyethylene glycol is available from industry sources as PEG 200, 300, 400, 540 Blend, 600, Methoxy 750, 1450, 3350 and 8000. Other suitable polyethylene glycols include those having a molecular weight (MW) within the range of about 200 to about 8,000. Fatty alcohols are aliphatic alcohols derived from natural fats and oils, originating in plants, but also synthesized in animals and algae. Fatty alcohols usually have an even number of carbon atoms. Production from fatty acids yields normal-chain alcohols—the alcohol group (—OH) attaches to the terminal carbon. Other processing can yield iso-alcohols—where the alcohol attaches to a carbon in the interior of the carbon chain. Useful fatty alcohols include $C_{4-34}$ saturated and unsaturated alcohols. Exemplary fatty alcohols include capryl alcohol (1-octanol), 2-ethyl hexanol, pelargonic alcohol (1-nonanol), capric alcohol (1-decanol, decyl alcohol), 1-dodecanol (lauryl alcohol), myristyl alcohol (1-tetradecanol), cetyl alcohol (1-hexadecanol), palmitoleyl alcohol (cis-9-hexadecan-1-ol), steryl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z,12Z-octadecadien-1-ol), elaidolinoleyl alcohol (9E,12E-octadecadien-1-ol), linolenyl alcohol (9Z,12Z,15Z-octadecadien-1-ol), elaidolinolenyl alcohol (9E,12E,15-E-octadecatrien-1-ol), ricinoleyl alcohol (12-hydroxy-9-octadecen-1-ol), arachidyl alcohol (1-eicosanol), behnyl alcohol (1-docosanol), erucyl alcohol (cis-13-docosen-1-ol), lignoceryl alcohol (1-tetracosanol), ceryl alcohol (1-hexacosanol), montanyl alcohol, cluytyl alcohol (1-octacosanol), myricyl alcohol, melissyl alcohol (1-triacontanol) and geddyl alcohol (1-tetratriacontanol). Polysaccharides are relatively complex carbohydrates, made up of many monosaccharides joined together by glycosidic bonds. Polysaccharides have a general formula of $C_n(H_2O)_{n-1}$ where n is usually a large number between 200 and 2500. Considering that the repeating units in the polymer backbone are often six-carbon monosaccharides, the general formula can also be represented as $(C_6H_{10}O_5)_n$ where n={40 . . . 3000}. Exemplary polysaccharides include chitosan. The excipients are generally contained in an amount of about 2-5 wt %.

It may be desirable to provide a relatively constant rate of release of the therapeutic agent from the drug delivery system over the life of the system. For example, it may be desirable for the therapeutic agent to be released in amounts from about 0.01 µg to about 2 µg per day for the life of the system. However, the release rate may change to either increase or decrease depending on the formulation of the biodegradable polymer matrix. In addition, the release profile of the therapeutic agent may include one or more linear portions and/or one or more non-linear portions. Preferably, the release rate is greater than zero once the system has begun to degrade or erode.

As discussed in the examples herein, the present drug delivery systems comprise a therapeutic component (a siRNA) and a polymeric component, as discussed above, which are associated to release an amount of the therapeutic agent that is effective in providing a concentration of the therapeutic agent in the vitreous of the eye in a range from about 0.2 nM to about 5 µM. In addition or alternatively, the present systems can release a therapeutically effective amount of the siRNA at a rate from about 0.003 g/day to about 5000 µg/day. As understood by persons of ordinary skill in the art, the desired release rate and target drug concentration will vary depending on the particular therapeutic agent chosen for the drug delivery system, the ocular condition being treated, and the patient's health. Optimization of the desired target drug concentration and release rate can be determined using routine methods known to persons of ordinary skill in the art.

The drug delivery systems, such as the intraocular implants, may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including the therapeutic agent(s) described herein, may be distributed in a non-homogenous pattern in the matrix. For example, the drug delivery system may include a portion that has a greater concentration of the therapeutic agent relative to a second portion of the system. The present drug delivery systems may be in the form of solid implants, semisolid implants, and viscoelastic implants, as discussed herein.

The intraocular implants disclosed herein may have a size of between about 5 mu.m and about 2 mm, or between about 10 mu.m and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm.times.0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 µg, more preferably about 500-1000 µg. For example, an implant may be about 500 µg, or about 1000 µg. However, larger implants may also be formed and further processed before administration to an eye. In addition, larger implants may be desirable where relatively greater amounts of a therapeutic agent are provided in the implant, as discussed in the examples herein. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Drug delivery systems can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The drug delivery systems may be of any geometry including fibers, sheets, films, microspheres, spheres, circular discs, plaques and the like. The upper limit for the system size will be determined by factors such as toleration for the system, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 µm to 4 mm in diameter, with comparable volumes for other shaped particles.

The size and form of the system can also be used to control the rate of release, period of treatment, and drug concentration at the site of implantation. For example, larger implants will deliver a proportionately larger dose, but depending on the surface to mass ratio, may have a slower release rate. The particular size and geometry of the system are chosen to suit the site of implantation.

The proportions of therapeutic agent, polymer, and any other modifiers may be empirically determined by formulating several implants, for example, with varying proportions of such ingredients. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37.degree. C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the therapeutic agent included in the intraocular drug delivery systems disclosed hereinabove, the systems may also include one or more additional ophthalmically acceptable therapeutic agents. For example, a system may include one or more antihistamines, one or more different antibiotics, one or more beta blockers, one or more steroids, one or more antineoplastic agents, one or more immunosuppressive agents, one or more antiviral agents, one or more antioxidant agents, and mixtures thereof.

Pharmacologic or therapeutic agents which may find use in the present systems, include, without limitation, those disclosed in U.S. Pat. No. 4,474,451, columns 4-6 and U.S. Pat. No. 4,327,725, columns 7-8.

Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, cyclosporine, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, gatifloxacin, ofloxacin, and derivatives thereof.

Examples of beta blockers include acebutolol, atenolol, labetalol, metoprolol, propranolol, timolol, and derivatives thereof.

Examples of steroids include corticosteroids, such as cortisone, prednisolone, fluorometholone, dexamethasone, medrysone, loteprednol, fluazacort, hydrocortisone, prednisone, betamethasone, beclomethasone, beclomethasone diproprionate, prednisone, methylprednisolone, riamcinolone hexacatonide, paramethasone acetate, diflorasone, fluocinonide, fluocinolone, triamcinolone, triamcinolone acetonide, derivatives thereof, and mixtures thereof.

Examples of antineoplastic agents include adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valciclovir, dideoxycytidine, phosphonoformic acid, ganciclovir and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, *Ginkgo Biloba* extract, tea catechins, bilberry extract, vitamins E or esters of vitamin E, retinyl palmitate, and derivatives thereof.

Other therapeutic agents include squalamine, carbonic anhydrase inhibitors, alpha agonists, prostamides, prostaglandins, antiparasitics, antifungals, and derivatives thereof.

The amount of active agent or agents employed in the drug delivery system, individually or in combination, will vary widely depending on the effective dosage required and the desired rate of release from the system. As indicated herein, the agent will be at least about 1, more usually at least about 10 weight percent of the system, and usually not more than about 80.

In addition, the drug delivery systems may include a solubility enhancing component provided in an amount effective to enhance the solubility of the therapeutic agent relative to substantially identical systems without the solubility enhancing component. For example, an implant may include β-cyclodextrin, which is effective in enhancing the solubility of the therapeutic agent. The β-cyclodextrin may be provided in an amount from about 0.5% (w/w) to about 25% (w/w) of the implant. In certain implants, the β-cyclodextrin is provided in an amount from about 5% (w/w) to about 15% (w/w) of the implant. Other implants may include a gamma-cyclodextrin, and/or cyclodextrin derivatives.

In some situations mixtures of drug delivery systems may be utilized employing the same or different pharmacological agents. In this way, a cocktail of release profiles, giving a biphasic or triphasic release with a single administration is achieved, where the pattern of release may be greatly varied. As one example, a mixture may comprise a plurality of polymeric microparticles and one or more implants.

Additionally, release modulators such as those described in U.S. Pat. No. 5,869,079 may be included in the drug delivery systems. The amount of release modulator employed will be dependent on the desired release profile, the activity of the modulator, and on the release profile of the therapeutic agent in the absence of modulator. Electrolytes such as sodium chloride and potassium chloride may also be included in the systems. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

In one embodiment, an intravitreal drug delivery system comprises a biodegradable polymer, such as PLGA, and a VEGF/VEGFR inhibitor (particularly a siRNA). The system can be in the form of a biodegradable intravitreal implant. The drug delivery system includes an amount of a VEGF/VEGFR inhibitor that when released from the system, the inhibitor can provide a therapeutic effect. For example, the biodegradable implant can comprise a siRNA that interferes with interactions between VEGF and VEGFR. Examples of useful inhibitors are described above. These drug delivery systems provide prolonged delivery of the VEGF inhibitor directly into the vitreous of an eye in need of treatment. Thus, these drug delivery systems can provide effective treatment of one or more ocular conditions, including without limitation, neovascularization, ocular tumors, and the like.

Embodiments of the present invention also relate to compositions comprising the present drug delivery systems. For example, and in one embodiment, a composition may comprise the present drug delivery system and an ophthalmically acceptable carrier component. Such a carrier component may be an aqueous composition, for example saline or a phosphate buffered liquid.

The present drug delivery systems are preferably administered to patients in a sterile form. For example, the present drug delivery systems, or compositions containing such systems, may be sterile when stored. Any routine suitable method of sterilization may be employed to sterilize the drug delivery systems. For example, the present systems may be sterilized using radiation. Preferably, the sterilization method does not reduce the activity or biological or therapeutic activity of the therapeutic agents of the present systems.

Various techniques may be employed to produce the drug delivery systems described herein. Useful techniques include, but are not necessarily limited to, solvent evaporation methods, phase separation methods, interfacial methods, molding methods, injection molding methods, extrusion methods, co-extrusion methods, carver press method, die cutting methods, heat compression, combinations thereof and the like.

Specific methods are discussed in U.S. Pat. No. 4,997,652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes. For example, a time period may be about 10 minutes, preferably about 0 to 5 min. The implants are then extruded at a temperature of about 60 degrees C. to about 130 degrees C., such as about 75 degrees C.

In addition, the implant may be coextruded so that a coating is formed over a core region during the manufacture of the implant.

Compression methods may be used to make the drug delivery systems, and typically yield elements with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

In certain embodiments of the present invention, a method of producing a sustained-release intraocular drug delivery system, comprises combining a non-neurotoxic macromolecule therapeutic agent and a polymeric material to form a drug delivery system suitable for placement in the interior of an eye of an individual. The resulting drug delivery system is effective in releasing the macromolecule therapeutic agent into the eye for at least about one week after the drug delivery system is placed in the eye. The method may comprise a step of extruding a particulate mixture of the macromolecule therapeutic agent and the polymeric material to form an extruded composition, such as a filament, sheet, and the like. The macromolecule preferably retains its biological activity when the macromolecule is released from the drug delivery system. For example, the macromolecule may be released having a structure that is identical or substantially identical to the native structure of the macromolecule under physiological conditions.

When polymeric particles are desired, the method may comprise forming the extruded composition into a population of polymeric particles or a population of implants, as described herein. Such methods may include one or more steps of cutting the extruded composition, milling the extruded composition, and the like.

As discussed herein, the polymeric material may comprise a biodegradable polymer, a non-biodegradable polymer, or a combination thereof. Examples of polymers and macromolecule therapeutic agents include each and every one of the polymers and agents identified above.

As discussed herein, the present systems may be configured to release the therapeutic agent into the eye at a rate from about 0.003 µg/day to about 5000 µg/day. Thus, the foregoing methods may combine the polymeric component and the therapeutic component to form a drug delivery system with such desirable release rates. In addition, the present systems can be configured to provide amounts of the therapeutic agent that are cleared from the vitreous at a desired target rate. As described in the examples, the clearance rates can range from about 3 mL/day to about 15 mL/day. However, certain implants can release therapeutically effective amounts of the therapeutic agent that are cleared from the vitreous at lower rates, such as less than about 1 mL/day.

As described herein, it has been discovered that the present systems can be formed by extruding a polymeric component/therapeutic component mixture without disrupting the biological activity of the macromolecule therapeutic agent. For example, implants have been invented which include a macromolecule that retains its structure after an extrusion process. Thus, in spite of the manufacturing conditions, drug delivery systems in accordance with the disclosure herein have been invented which include biologically active macromolecules.

The drug delivery systems of the present invention may be inserted into the eye, for example the vitreous chamber of the eye, by a variety of methods, including intravitreal injection or surgical implantation. For example, the drug delivery systems may be placed in the eye using forceps or a trocar after making a 2-3 mm incision in the sclera. Preferably, the present systems can be placed in an eye without making an incision. For example, the present systems may be placed in an eye by inserting a trocar or other delivery device directly through the eye without an incision. The removal of the device after the placement of the system in the eye can result in a self-sealing opening. One example of a device that may be used to insert the implants into an eye is disclosed in U.S. Patent Publication No. 2004/0054374. The method of placement may influence the therapeutic component or drug release kinetics. For example, delivering the system with a trocar may result in placement of the system deeper within the vitreous than placement by forceps, which may result in the system being closer to the edge of the vitreous. The location of the system may influence the concentration gradients of therapeutic component or drug surrounding the element, and thus influence the release rates (e.g., an element placed closer to the edge of the vitreous may result in a slower release.

The present systems are configured to release an amount of the therapeutic agent effective to treat or reduce a symptom of an ocular condition, such as an ocular condition such as glaucoma or edema. More specifically, the systems may be used in a method to treat or reduce one or more symptoms of glaucoma or proliferative vitreoretinopathy.

The systems disclosed herein may also be configured to release additional therapeutic agents, as described above, which to prevent diseases or conditions, such as the following:

Maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (PONS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

In one embodiment, an implant is administered to a posterior segment of an eye of a human or animal patient, and preferably, a living human or animal. In at least one embodiment, an implant is administered without accessing the subretinal space of the eye. However, in other embodiments the implant may be inserted into the subretinal space. For example, a method of treating a patient may include placing the implant directly into the posterior chamber of the eye. In other embodiments, a method of treating a patient may comprise administering an implant to the patient by at least one of intravitreal placement, subretinal placement, subconjuctival placement, sub-tenon placement, retrobulbar placement, and suprachoroidal placement. Placement methods may include injection and/or surgical insertion.

In at least one embodiment, a method of reducing neovascularization or angiogenesis in a patient comprises administering one or more implants containing one or more therapeutic agents, as disclosed herein to a patient by at least one of intravitreal injection, subconjuctival injection, sub-tenon injection, retrobulbar injection, and suprachoroidal injection. A syringe apparatus including an appropriately sized needle, for example, a 22 gauge needle, a 27 gauge needle or a 30 gauge needle, can be effectively used to inject the composition with the posterior segment of an eye of a human or animal. Repeat injections are often not necessary due to the extended release of the therapeutic agent from the implants.

In another aspect of the invention, kits for treating an ocular condition of the eye are provided, comprising: a) a container comprising an extended release implant comprising a therapeutic component including a therapeutic agent as herein described, and a drug release sustaining component; and b) instructions for use. Instructions may include steps of how to handle the implants, how to insert the implants into an ocular region, and what to expect from using the implants.

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or a combination of both. It may be understood that the polymeric component of the present systems is associated with the therapeutic component so that the release of the therapeutic component into the eye is by one or more of diffusion, erosion, dissolution, and osmosis. As discussed herein, the matrix of an intraocular drug delivery system may release drug at a rate effective to sustain release of an amount of the therapeutic agent for more than one week after implantation into an eye. In certain systems, therapeutic amounts of the therapeutic agent are released for more than about one month, and even for about twelve months or more. For example, the therapeutic component can be released into the eye for a time period from about ninety days to about one year after the system is placed in the interior of an eye.

The release of the therapeutic agent from the intraocular systems comprising a biodegradable polymer matrix may include an initial burst of release followed by a gradual increase in the amount of the therapeutic agent released, or the release may include an initial delay in release of the therapeutic agent followed by an increase in release. When the system is substantially completely degraded, the percent of the therapeutic agent that has been released is about one hundred. Compared to existing implants, the systems disclosed herein do not completely release, or release about 100% of the therapeutic agent, until after about one month of being placed in an eye.

It may be desirable to provide a relatively constant rate of release of the therapeutic agent from the drug delivery system over the life of the system. For example, it may be desirable for the therapeutic agent to be released in amounts from about 0.01 pg to about 2 pg per day for the life of the system. However, the release rate may change to either increase or decrease depending on the formulation of the biodegradable polymer matrix. In addition, the release profile of the therapeutic agent may include one or more linear portions and/or one or more non-linear portions. Preferably, the release rate is greater than zero once the system has begun to degrade or erode.

As discussed in the examples herein, the present drug delivery systems comprise a therapeutic component and a polymeric component, as discussed above, which are associated to release an amount of the therapeutic siRNA agent that is effective in providing a concentration of the therapeutic agent in the vitreous of the eye for treating the desired condition, for example in a range from about 0.2 nM to about 5 pM. In addition or alternatively, the present systems can release a therapeutically effective amount of the siRNA molecule at a rate from about 0.003 pg/day to about 5000 pg/day. As understood by persons of ordinary skill in the art, the desired release rate and target drug concentration will vary depending on the particular therapeutic agent chosen for the drug delivery system, the ocular condition being treated, and the patient's health. Optimization of the desired target drug concentration and release rate can be determined using routine methods known to persons of ordinary skill in the art.

In addition to the therapeutic component, the intraocular drug delivery systems disclosed herein may include an excipient component, such as effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between about 2 to about 9, and more preferably about 4 to about 8. As such the buffering agent may be as much as about 5% by weight of the total system. These agents may be present in amounts of from 0.001 to about 5% by weight and preferably 0.01 to about 2% by weight.

In some situations mixtures of drug delivery systems may be utilized employing the same or different pharmacological agents. In this way, a cocktail of release profiles, giving a biphasic or triphasic release with a single administration is achieved, where the pattern of release may be greatly varied.

In another embodiment, a delivery system comprises a biodegradable polymer, such as PLGA, and a VEGFNEGFR inhibitor. The system can be in the form of a population of biodegradable polymeric nanoparticles. The drug delivery system includes an amount of a VEGFNEGFR inhibitor that when released from the system, the inhibitor can provide a therapeutic effect. These drug delivery systems provide prolonged delivery of the VEGF inhibitor directly into the vitreous of an eye in need of treatment. Thus, these drug delivery systems can provide effective treatment of one or more ocular conditions, including without limitation, neovascularization, ocular tumors, and the like.

Embodiments of the present invention also relate to compositions comprising the present drug delivery systems. For example, and in one embodiment, a composition may comprise the present drug delivery system and an ophthalmically acceptable carrier component. Such a carrier component may be an aqueous composition, for example saline or a phosphate buffered liquid.

The present drug delivery systems are preferably administered to patients in a sterile form. For example, the present drug delivery systems, or compositions containing such systems, may be sterile when stored. Any routine suitable method of sterilization may be employed to sterilize the drug delivery-systems. For example, the present systems may be sterilized using radiation. Preferably, the sterilization method does not reduce the activity or biological or therapeutic activity of the therapeutic agents of the present systems, and lyophilization of the NPs of the invention may be employed to this end.

The drug delivery systems can be sterilized by gamma irradiation. As an example, the particles can be sterilized by 2.5 to 4.0 mrad of gamma irradiation. The particles can be terminally sterilized in their final primary packaging system including administration device e.g. syringe applicator. Alternatively, the particles can be sterilized alone and then aseptically packaged into an applicator system. In this case the applicator system can be sterilized by gamma irradiation, ethylene oxide (ETO), heat or other means. The drug delivery systems can be sterilized by gamma irradiation at low temperatures to improve stability or blanketed with argon, nitrogen or other means to remove oxygen. Beta irradiation or e-beam may also be used to sterilize the particles as well as UV irradiation. The dose of irradiation from any source can be lowered depending on the initial bioburden of the particles such that it may be much less than 2.5 to 4.0 mrad. The drug delivery systems may be manufactured under aseptic conditions from sterile starting components. The starting components may be sterilized by heat, irradiation (gamma, beta, UV), ETO or sterile filtration. Semi-solid polymers or solutions of polymers may be sterilized prior to drug delivery system fabrication and macromolecule incorporation by sterile filtration of heat. The sterilized polymers can then be used to aseptically produce sterile drug delivery systems.

The drug delivery systems of the present invention may be inserted into the eye, for example the vitreous chamber of the eye, by a variety of methods, including intravitreal injection, such as with pre-filled syringes in ready-to-inject form for use by medical personnel. The location of the system may influence the concentration gradients of therapeutic component or drug surrounding the element, and thus influence the release rates (e.g., an element placed closer to the edge of the vitreous may result in a slower release rate). The hydrogel suspensions can be administered via standard known needles, such as 27 g or 30 g needles, delivering up to about 1.5 mg siRNA per dose, depending upon the condition to be treated.

The present systems are configured to release an amount of the therapeutic agent effective to treat or reduce a symptom of an ocular condition, such as an ocular condition such as glaucoma or edema. More specifically, the systems may be used in a method to treat or reduce one or more symptoms of glaucoma or proliferative vitreoretinopathy.

In another aspect of the invention, kits for treating an ocular condition of the eye are provided, comprising: a) a container comprising an extended release implant comprising a therapeutic component including a therapeutic agent as herein described, and a drug release sustaining component; and b) instructions for use. Instructions may include steps of how to handle the drug delivery system of the invention, how to administer the drug delivery system of the invention into an ocular region, and what to expect from using the implants.

3. EXAMPLES

The following non-limiting examples provide those of ordinary skill in the art with specific preferred drug delivery systems and methods for making such systems.

Example 1

Manufacture and Testing of Implants Containing a Therapeutic Agent and a Biodegradable Polymer Matrix Biodegradable implants are made by combining a therapeutic agent, such as those agents described above, with a biodegradable polymer composition in a stainless steel mortar. The combination is mixed via a Turbula shaker set at 96 RPM for 15 minutes. The powder blend is scraped off the wall of the mortar and then remixed for an additional 15 minutes. The mixed powder blend is heated to a semi-molten state at specified temperature for a total of 30 minutes, forming a polymer/drug melt.

Rods are manufactured by pelletizing the polymer/drug melt using a 9 gauge polytetrafluoroethylene (PTFE) tubing, loading the pellet into the barrel and extruding the material at the specified core extrusion temperature into filaments. The filaments are then cut into about 1 mg size implants or drug delivery systems. The rods have dimensions of about 2 mm long×0.72 mm diameter. The rod implants weigh between about 900 μg and 1100 μg.

Wafers are formed by flattening the polymer melt with a Carver press at a specified temperature and cutting the flattened material into wafers, each weighing about 1 mg. The wafers have a diameter of about 2.5 mm and a thickness of about 0.13 mm. The wafer implants weigh between about 900 μg and 1100 μg.

In-vitro release testing can be performed on each lot of implant (rod or wafer). Each implant may be placed into a 24 mL screw cap vial with 10 mL of Phosphate Buffered Saline solution at 37° C. and 1 mL aliquots are removed and replaced with equal volume of fresh medium on day 1, 4, 7, 14, 28, and every two weeks thereafter.

Drug assays may be performed by HPLC, which consists of a Waters 2690 Separation Module (or 2696), and a Waters 2996 Photodiode Array Detector. An Ultrasphere, C-18 (2), 5 mm; 4.6×150 mm column heated at 30.degree. C. can be used for separation and the detector can be set at 264 nm. The mobile phase can be (10:90) MeOH-buffered mobile phase with a flow rate of 1 mL/min and a total run time of 12 min per sample. The buffered mobile phase may comprise (68:0.75:0.25:31) 13 mM 1-Heptane Sulfonic Acid, sodium salt-glacial acetic acid-triethylamine-Methanol. The release rates can be determined by calculating the amount of drug being released in a given volume of medium over time in mg/day.

The polymers chosen for the implants can be obtained from Boehringer Ingelheim or Purac America, for example. Examples of polymers include: RG502, RG752, R202H, R203 and R206, and Purac PDLG (50/50). RG502 is (50:50) poly(D,L-lactide-co-glycolide), RG752 is (75:25) poly(D,L-lactide-co-glycolide), R202H is 100% poly(D, L-lactide) with acid end group or terminal acid groups, R203 and R206 are both 100% poly(D, L-lactide). Purac PDLG (50/50) is (50:50) poly(D,L-lactide-co-glycolide). The inherent viscosity of RG502, RG752, R202H, R203, R206, and Purac PDLG are 0.2, 0.2, 0.2, 0.3, 1.0, and 0.2 dL/g, respectively. The average molecular weight of RG502, RG752, R202H, R203, R206, and Purac PDLG are, 11700, 11200, 6500, 14000, 63300, and 9700 daltons, respectively.

Example 2

Polymeric Drug Delivery Systems Containing Cand5

Drug delivery systems which comprise about 86.1 milligrams of Cand5 can be produced similar to those systems described in Examples 1. Such drug delivery systems release Cand5 at a rate from about 49.7 micrograms per day to about 4970 micrograms per day. The release rates can be measured using in vitro and/or in vivo assays as described above. Placement of the Cand5 drug delivery systems into the vitreous of an eye provide therapeutic benefits, such as the treatment of neovascularization and the like, for at least about thirty days after a single administration. Improvements in patient function, such as vision and intraocular pressure, can be observed at longer time periods.

Example 3

Polymeric Drug Delivery Systems Containing siRNA Z

Drug delivery systems which comprise about 86.1 milligrams of siRNA Z can be produced similar to those systems described in Examples 1, above. Such drug delivery systems release siRNA Z at a rate from about 49.7 micrograms per day to about 4970 micrograms per day. The release rates can be measured using in vitro and/or in vivo assays as described above. Placement of the siRNA Z drug delivery systems into the vitreous of an eye provide therapeutic benefits, such as the treatment of neovascularization and the like, for at least about thirty days after a single administration. Improvements in patient function, such as vision and intraocular pressure, can be observed at longer time periods.

Example 4

Sustained Release of Sima027 from PLGA Implants

Implants are prepared as described above and composed 10-20% Sima027, 2-5% cholesterol (C75209 from Sigma-Aldrich) or PEG3350, and either single PLGA polymer or double PLGA polymer blends.

For the formulations containing PEG3350 as excipient, PEG3350 and Sima027 are first co-dissolved and mixed in water. Such aqueous blends are lyophilized to dry powder before being blended with PLGA polymers. The powder blends are further processed to implant filaments through hot melt extrusion.

For the formulations containing cholesterol as excipient, all components are mixed and blended as powder prior to hot melt extrusion.

The Analytical Method for In Vitro Release Study of Sima027 PLGA Implants:

Sima027 implants are cut into 5-6 mm pieces and 4 pieces from each formulation are placed in 2 ml of PBS solution for in vitro release study. Each formulation is analyzed in duplicate. The vials are placed in 37° C. water batch with gentle shaking and at various time-points, the solutions in the vials are collected and replaced with fresh solutions. The amounts of Sima027 released from implants are analyzed by HPLC method with detection at 260 nm.

The In Vitro Release Profiles of Sima027 PLGA Implants:

The release of Sima027 from PEG3350 containing-implants can be controlled by various PLGA polymer blending ratios. FIG. 1 shows the results of in vitro release profile studies for a 10% Sima027 implant, with the noted variations in PEG concentrations; wherein the samples A1-A5 in FIG. 1 comprise 10% (w/w) Sima027 and the following components:

A1—5% (w/w) PEG3350 as excipient in a polymeric component comprised of 100% RG752S.

A2—5% (w/w) PEG3350 as excipient in a polymeric component comprised of 94% RG752S and 6% RG502H.

A3—5% (w/w) PEG3350 as excipient in a polymeric component comprised of 50% RG752S and 50% R203H.

A4—5% (w/w) PEG3350 as excipient in a polymeric component comprised of 100% RG502H.

A5—5% (w/w) PEG1450 as excipient in a polymeric component comprised of 100% RG752S.

Figure 2:
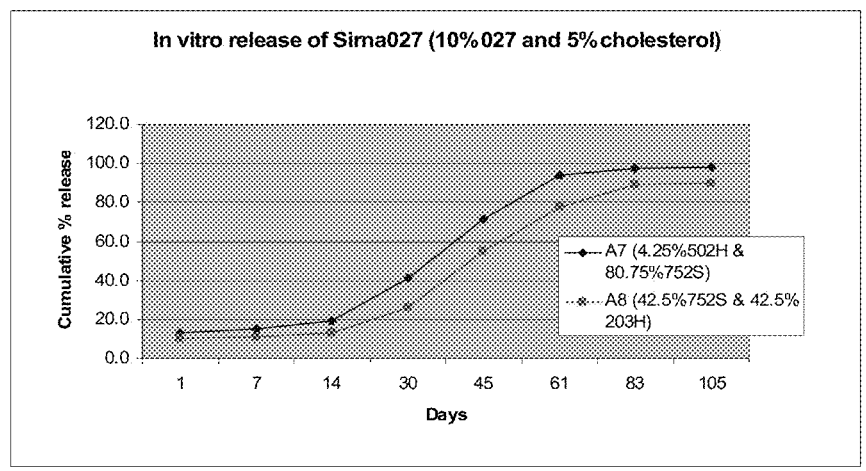

FIG. 2 shows the results of an in vitro release study with PLGA implants containing 10% Sima027 and 5% cholesterol; wherein the samples A7 and A8 in FIG. 2 comprise 10% (w/w) Sima027 and the following components:

A7—5% (w/w) cholesterol as excipient, in combination with 4.25% (w/w) of RG502H and 80.75% (w/w) of RG752S as the polymeric component.

A8—5% (w/w) cholesterol as excipient, in combination with 42.5% (w/w) of RG752S and 42.5% (w/w) of R203H as the polymeric component.

Figure 3A:
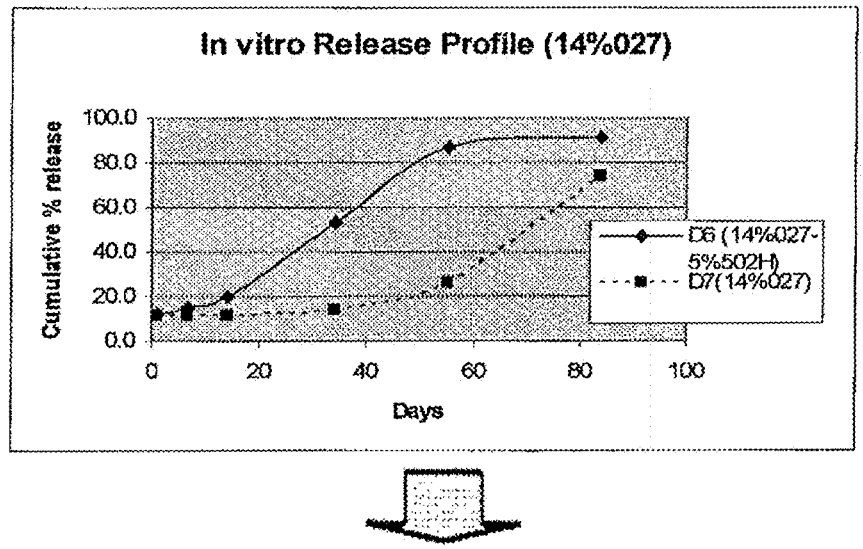

FIGS. 3A and B show the results of an in vitro release study on PLGA implants containing 14% Sima027 and 2%

PEG3350; wherein the samples D6 and D7 in FIG. 3 comprise 14% Sima027 and the following components:

D6—2% (w/w) PEG3350 as excipient, in combination with 5% (w/w) of RG502H and 79% (w/w) of RG752S as the polymeric component.

D7—2% (w/w) PEG3350 as excipient, in combination with 84% (w/w) of RG752S as the polymeric component.

Figure 3B:
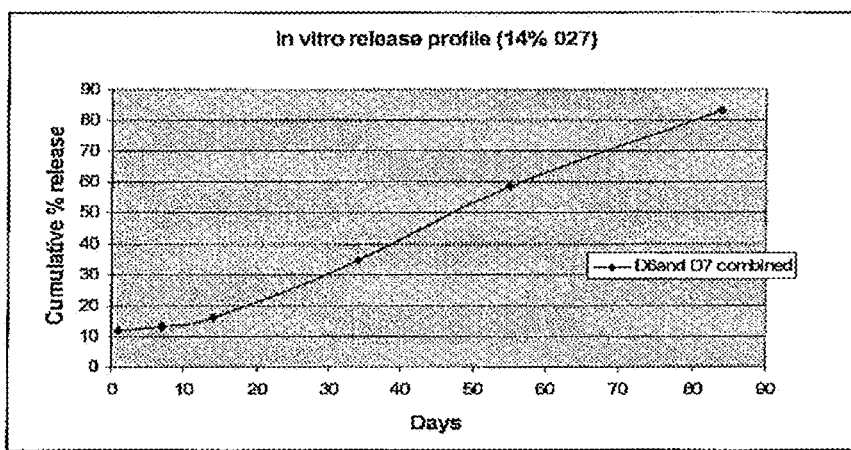

The graph in FIG. 3B shows the mathematically determined release profile for a composite of D6 and D7.

Figure 4A:
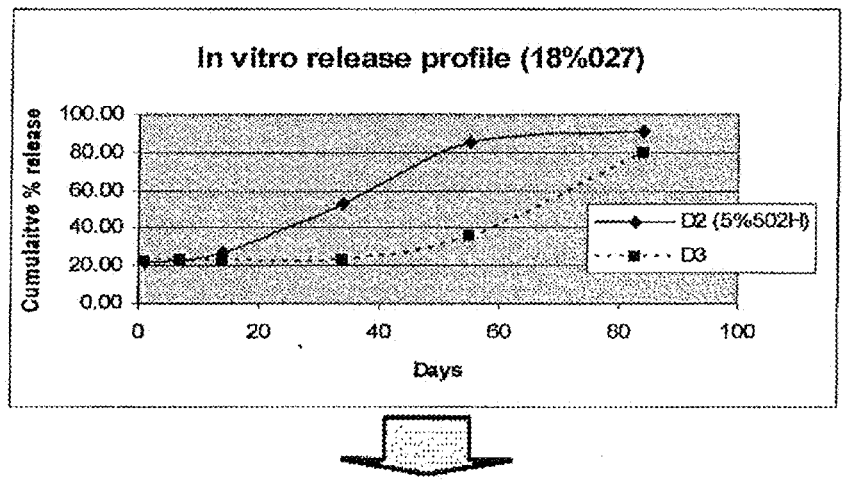

FIGS. 4A and B show the results of an in vitro release study on PLGA implants containing 18% Sima027 and 2% PEG; wherein the samples D2 and D3 in FIG. 4 comprise 18% Sima027 and the following components:

D2—2% (w/w) PEG3350 as excipient, in combination with 5% (w/w) of RG502H and 79% (w/w) of RG752S as the polymeric component.

D3—2% (w/w) PEG3350 as excipient, in combination with 84% (w/w) of RG752S as the polymeric component.

Figure 4B:
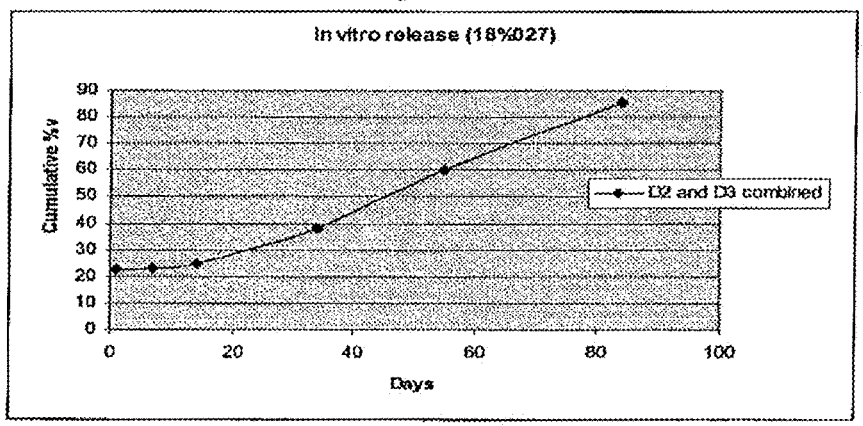

The graph in FIG. 4B shows the mathematically determined release profile for a composite of D2 and D3.

The present invention also encompasses the use of any and all possible combinations of the therapeutic agents disclosed herein in the manufacture of a medicament, such as a drug delivery system or composition comprising such a drug delivery system, to treat one or more ocular conditions, including those identified above.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

What is claimed is:

1. A sustained release, biodegradable intraocular implant comprising a) about 70-85% by weight of a biodegradable polymeric carrier, wherein the biodegradable polymeric carrier is a poly-lactide-co-glycolide (PLGA) co-polymer; b) about 10-20% by weight of a water soluble therapeutic agent, wherein the therapeutic agent is an inhibitor of vascular endothelial growth factor (VEGF) selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 2 and the exactly complementary nucleotide sequences to each of these sequences; and c) about 5-10% by weight of a long chain fatty alcohol comprising from between 10 to 40 carbon atoms; wherein a therapeutically effective amount of the therapeutic agent is released from the biodegradable intraocular implant for at least one week after the intraocular implant is placed in the eye.

2. The intraocular implant of claim 1, wherein the long chain fatty alcohol is selected from the group consisting of capric alcohol, lauryl alcohol, myristyl alcohol, cetyl alcohol, palmitoleyl alcohol, stearyl alcohol, isostearyl alcohol, elaidyl alcohol, oleyl alcohol, linoleyl alcohol, polyunsaturated elaidolinoleyl alcohol, polyunsaturated linolenyl alcohol, elaidolinolenyl alcohol, polyunsaturated ricinoleyl alcohol, arachidyl alcohol, behenyl alcohol, erucyl alcohol, lignoceryl alcohol, ceryl alcohol, montanyl alcohol, cluytyl alcohol, myricyl alcohol, melissyl alcohol, and geddyl alcohol.

3. A method for treating an ocular condition, the method comprising the step of intraocular placement of a sustained release, biodegradable intraocular implant according to claim 1.

4. The method of claim 3, wherein the step of intraocular placement is carried out using an intraocular injector.

5. The method of claim 3, wherein the ocular condition is selected from the group consisting of uveitis, macular edema, macular degeneration, proliferative retinopathy, diabetic retinopathy, retinitis pigmentosa and glaucoma.

6. The intraocular implant of claim 1, wherein said long chain fatty alcohol is selected from the group consisting of 1-hexadecanol, 1-octadecanol, and 1-eicosanol.

7. The intraocular implant of claim 1, wherein said long chain fatty alcohol is a saturated straight chain alcohol 16 to 26 carbon atoms in length.

8. The intraocular implant of claim 7, wherein said long chain fatty alcohol is 1-eicosanol.

* * * * *

SEQUENCE LISTING

<160> NUMBER OF SEQ ID NOS: 8

<210> SEQ ID NO 1
<211> LENGTH: 576
<212> TYPE: DNA
<213> ORGANISM: Homo sapiens

<400> SEQUENCE: 1

| | | | | | |
|---|---|---|---|---|---|
| atgaactttc | tgctgtcttg | ggtgcattgg | agccttgcct | tgctgctcta | cctccaccat | 60 |
| gccaagtggt | cccaggctgc | acccatggca | gaaggaggag | ggcagaatca | tcacgaagtg | 120 |
| gtgaagttca | tggatgtcta | tcagcgcagc | tactgccatc | caatcgagac | cctggtggac | 180 |
| atcttccagg | agtaccctga | tgagatcgag | tacatcttca | agccatcctg | tgtgcccctg | 240 |
| atgcgatgcg | ggggctgctg | caatgacgag | ggcctggagt | gtgtgcccac | tgaggagtcc | 300 |
| aacatcacca | tgcagattat | gcggatcaaa | cctcaccaag | gccagcacat | aggagagatg | 360 |
| agcttcctac | agcacaacaa | atgtgaatgc | agaccaaaga | aagatagagc | aagacaagaa | 420 |
| aatccctgtg | ggccttgctc | agagcggaga | aagcatttgt | ttgtacaaga | tccgcagacg | 480 |
| tgtaaatgtt | cctgcaaaaa | cacagactcg | cgttgcaagg | cgaggcagct | tgagttaaac | 540 |
| gaacgtactt | gcagatgtga | caagccgagg | cggtga | | | 576 |

<210> SEQ ID NO 2
<211> LENGTH: 4071
<212> TYPE: DNA
<213> ORGANISM: Homo Sapiens

<400> SEQUENCE: 2

| | | | | | |
|---|---|---|---|---|---|
| atggagagca | aggtgctgct | ggccgtcgcc | ctgtggctct | gcgtggagac | ccgggccgcc | 60 |
| tctgtgggtt | tgcctagtgt | ttctcttgat | ctgcccaggc | tcagcataca | aaaagacata | 120 |
| cttacaatta | aggctaatac | aactcttcaa | attacttgca | ggggacagag | ggacttggac | 180 |
| tggctttggc | ccaataatca | gagtggcagt | gagcaaaggg | tggaggtgac | tgagtgcagc | 240 |
| gatggcctct | tctgtaagac | actcacaatt | ccaaaagtga | tcggaaatga | cactggagcc | 300 |
| tacaagtgct | tctaccggga | aactgacttg | gcctcggtca | tttatgtcta | tgttcaagat | 360 |
| tacagatctc | catttattgc | ttctgttagt | gaccaacatg | gagtcgtgta | cattactgag | 420 |
| aacaaaaaca | aaactgtggt | gattccatgt | ctcgggtcca | tttcaaatct | caacgtgtca | 480 |
| ctttgtgcaa | gatacccaga | aaagagattt | gttcctgatg | gtaacagaat | ttcctgggac | 540 |

```
agcaagaagg gctttactat tcccagctac atgatcagct atgctggcat ggtcttctgt    600
gaagcaaaaa ttaatgatga aagttaccag tctattatgt acatagttgt cgttgtaggg    660
tataggattt atgatgtggt tctgagtccg tctcatggaa ttgaactatc tgttggagaa    720
aagcttgtct taaattgtac agcaagaact gaactaaatg tggggattga cttcaactgg    780
gaatacccct cttcgaagca tcagcataag aaacttgtaa accgagacct aaaaacccag    840
tctgggagtg agatgaagaa attttttgagc accttaacta tagatggtgt aacccggagt    900
gaccaaggat tgtacacctg tgcagcatcc agtgggctga tgaccaagaa gaacagcaca    960
tttgtcaggg tccatgaaaa acctttttgtt gcttttggaa gtggcatgga atctctggtg   1020
gaagccacgg tgggggagcg tgtcagaatc cctgcgaagt accttggtta ccccaccccca   1080
gaaataaaat ggtataaaaa tggaataccc cttgagtcca atcacacaat aaagcgggg    1140
catgtactga cgattatgga agtgagtgaa agagacacag gaaattacac tgtcatcctt   1200
accaatccca tttcaaagga gaagcagagc catgtggtct ctctggttgt gtatgtccca   1260
ccccagattg gtgagaaatc tctaatctct cctgtggatt cctaccagta cggcaccact   1320
caaacgctga catgtacggt ctatgccatt cctccccccgc atcacatcca ctggtattgg   1380
cagttggagg aagagtgcgc caacgagccc agccaagctg tctcagtgac aaacccatac   1440
ccttgtgaag aatggagaag tgtggaggac ttccagggag gaaataaaat tgaagttaat   1500
aaaaatcaat ttgctctaat tgaaggaaaa aacaaaactg taagtaccct tgttatccaa   1560
gcggcaaatg tgtcagcttt gtacaaatgt gaagcggtca acaaagtcgg gagaggagag   1620
agggtgatct ccttccacgt gaccagggt cctgaaatta ctttgcaacc tgacatgcag   1680
cccactgagc aggagagcgt gtcttttgtgg tgcactgcag acagatctac gtttgagaac   1740
ctcacatggt acaagcttgg cccacagcct ctgccaatcc atgtgggaga gttgcccaca   1800
cctgtttgca agaacttgga tactcttttgg aaattgaatg ccaccatgtt ctctaatagc   1860
acaaatgaca ttttgatcat ggagcttaag aatgcatcct gcaggacca aggagactat   1920
gtctgccttg ctcaagacag gaagaccaag aaaagacatt gcgtggtcag gcagctcaca   1980
gtcctagagc gtgtggcacc cacgatcaca ggaaacctgg agaatcagac gacaagtatt   2040
ggggaaagca tcgaagtctc atgcacggca tctgggaatc cccctccaca gatcatgtgg   2100
tttaaagata atgagaccct tgtagaagac tcaggcattg tattgaagga tgggaaccgg   2160
aacctcacta tccgcagagt gaggaaggag gacgaaggcc tctacacctg ccaggcatgc   2220
agtgttcttg gctgtgcaaa agtggaggca tttttcataa tagaaggtgc ccaggaaaag   2280
acgaacttgg aaatcattat tctagtaggc acggcggtga ttgccatgtt cttctggcta   2340
cttcttgtca tcatcctacg gaccgttaag cgggccaatg gaggggaact gaagacaggc   2400
tacttgtcca tcgtcatgga tccagatgaa ctcccattgg atgaacattg tgaacgactg   2460
ccttatgatg ccagcaaatg ggaattcccc agagaccggc tgaagctagg taagcctctt   2520
ggccgtggtg cctttggcca agtgattgaa gcagatgcct ttggaattga caagacagca   2580
acttgcagga cagtagcagt caaaatgttg aaagaaggag caacacacag tgagcatcga   2640
gctctcatgt ctgaactcaa gatcctcatt catattggtc accatctcaa tgtggtcaac   2700
cttcaggtg cctgtaccaa gccaggaggg ccactcatgg tgattgtgga attctgcaaa   2760
tttggaaacc tgtccactta cctgaggagc aagagaaatg aatttgtccc ctacaagacc   2820
aaaggggcac gattccgtca agggaaagac tacgttggag caatcccctgt ggatctgaaa   2880
cggcgcttgg acagcatcac cagtagccag agctcagcca gctctggatt tgtggaggag   2940
```

-continued

```
aagtccctca gtgatgtaga agaagaggaa gctcctgaag atctgtataa ggacttcctg    3000
accttggagc atctcatctg ttacagcttc caagtggcta agggcatgga gttcttggca    3060
tcgcgaaagt gtatccacag ggacctggcg gcacgaaata tcctcttatc ggagaagaac    3120
gtggttaaaa tctgtgactt tggcttggcc cgggatattt ataaagatcc agattatgtc    3180
agaaaaggag atgctcgcct ccctttgaaa tggatggccc cagaaacaat ttttgacaga    3240
gtgtacacaa tccagagtga cgtctggtct tttggtgttt tgctgtggga aatatttcc    3300 ttaggtgctt ctccatatcc tggggtaaag attgatgaag aattttgtag gcgattgaaa    3360
gaaggaacta gaatgagggc ccctgattat actacaccag aaatgtacca gaccatgctg    3420
gactgctggc acggggagcc cagtcagaga cccacgtttt cagagttggt ggaacatttg    3480
ggaaatctct tgcaagctaa tgctcagcag gatggcaaag actacattgt tcttccgata    3540
tcagagactt tgagcatgga agaggattct ggactctctc tgcctacctc acctgtttcc    3600
tgtatggagg aggaggaagt atgtgacccc aaattccatt atgacaacac agcaggaatc    3660
agtcagtatc tgcagaacag taagcgaaag agccggcctg tgagtgtaaa aacatttgaa    3720
gatatcccgt tagaagaacc agaagtaaaa gtaatcccag atgacaacca gacggacagt    3780
ggtatggttc ttgcctcaga agagctgaaa actttggaag acagaaccaa attatctcca    3840
tcttttggtg gaatggtgcc cagcaaaagc agggagtctg tggcatctga aggctcaaac    3900
cagacaagcg gctaccagtc cggatatcac tccgatgaca cagacaccac cgtgtactcc    3960
agtgaggaag cagaactttt aaagctgata gagattggag tgcaaaccgg tagcacagcc    4020
cagattctcc agcctgactc ggggaccaca ctgagctctc tcctgtttta a              4071
```

<210> SEQ ID NO 3
<211> LENGTH: 19
<212> TYPE: RNA
<213> ORGANISM: Homo Sapiens
<220> FEATURE:
<223> OTHER INFORMATION: Sense strand of Cand5 siRNA

<400> SEQUENCE: 3
accucaccaa ggccagcac                                                   19

<210> SEQ ID NO 4
<211> LENGTH: 19
<212> TYPE: RNA
<213> ORGANISM: Homo Sapiens
<220> FEATURE:
<223> OTHER INFORMATION: Antisense strand for Cand5 siRNA

<400> SEQUENCE: 4
gugcuggccu uggugaggu                                                   19

<210> SEQ ID NO 5
<211> LENGTH: 19
<212> TYPE: RNA
<213> ORGANISM: Homo Sapiens
<220> FEATURE:
<223> OTHER INFORMATION: Sense strand of siRNA-027

<400> SEQUENCE: 5
cugaguuuaa aaggcaccc                                                   19

<210> SEQ ID NO 6
<211> LENGTH: 19
<212> TYPE: RNA
<213> ORGANISM: Homo Sapiens
<220> FEATURE:

```
<223> OTHER INFORMATION: Antisense strand for siRNA-027

<400> SEQUENCE: 6
gggugccuuu uaaacucag                                             19

<210> SEQ ID NO 7
<211> LENGTH: 23
<212> TYPE: DNA
<213> ORGANISM: Homo Sapiens
<220> FEATURE:
<221> NAME/KEY: misc_RNA
<222> LOCATION: (1)..(1)
<223> OTHER INFORMATION: inverted 2'-deoxy abasic nucleotide
<220> FEATURE:
<221> NAME/KEY: misc_RNA
<222> LOCATION: (23)..(23)
<223> OTHER INFORMATION: inverted 2'-deoxy abasic nucleotide

<400> SEQUENCE: 7
ncugaguuua aaaggcaccc ttn                                        23

<210> SEQ ID NO 8
<211> LENGTH: 21
<212> TYPE: DNA
<213> ORGANISM: Homo Sapiens
<220> FEATURE:
<223> OTHER INFORMATION: Antisense strand of Chemically modified siRNA-
      027

<400> SEQUENCE: 8
ttgacucaaa uuuuccgugg g                                          21
```